| United States Patent [19] | [11] | 4,439,445 |
|---|---|---|
| Robert et al. | [45] | Mar. 27, 1984 |

[54] CYTOPROTECTIVE USE OF OXAMATE DERIVATIVES

[75] Inventors: Andre Robert; Cleo Lancaster, both of Kalamazoo County, Mich.

[73] Assignee: The Upjohn Company, Kalamazoo, Mich.

[21] Appl. No.: 366,818

[22] Filed: Apr. 8, 1982

[51] Int. Cl.³ .................. A61K 31/275; A61K 31/24; A61K 31/195; A61K 31/44

[52] U.S. Cl. .................................... 424/304; 424/309; 424/319; 424/263

[58] Field of Search ............... 424/263, 304, 319, 309

[56] References Cited

U.S. PATENT DOCUMENTS

| 4,137,325 | 1/1979 | Sellstedt et al. | 424/311 |
| 4,152,448 | 5/1979 | Wardell | 424/283 |
| 4,186,127 | 1/1980 | Hall et al. | 424/244 |

*Primary Examiner*—Frederick E. Waddell
*Attorney, Agent, or Firm*—Lawrence T. Welch

[57] ABSTRACT

The present invention provides a method for gastrointestinal cytoprotection using a class of oxamic acids and derivatives thereof.

3 Claims, No Drawings

CYTOPROTECTIVE USE OF OXAMATE DERIVATIVES

DESCRIPTION

BACKGROUND OF THE INVENTION

The present invention provides a new use of known pharmacological agents. In particular, the present invention comprises the use of certain oxamate derivatives for the prophylaxis of certain diseases of the stomach, the duodenum, and the intestine.

Agents which are useful in the prophylaxis and treatment of gastrointestinal diseases are sometimes referred to as cytoprotective agents. A number of cytoprotective agents are known. U.S. Pat. No. 4,097,603 described the use of certain prostaglandins for gastric cytoprotection. For a brief history of cytoprotection, see Robert, Prostaglandins (supplement) 21:89–96 (1981).

PRIOR ART

Gastric cytoprotection methods are disclosed, for example, in U.S. Pat. No. 4,083,998 (Robert, "Treatment of Inflammatory Disease of the Mammalian Large Intestine with Cytoprotective Prostaglandins"), issued Apr. 11, 1978, U.S. Pat. No. 4,081,553 (Robert, "Cytoprotective Prostaglandins for Use in Intestinal Diseases"), issued Mar. 28, 1978; U.S. Pat. No. 4,097,603 (Robert, "Gastric Cytoprotection with Non-Antisecretory Doses of Prostaglandins"), issued June 27, 1978; and U.S. Pat. No. 3,917,828 (Robert, "Method of Reducing the Undesirable Gastrointestinal Effects of Prostaglandin Synthetase Inhibitors"), issued Nov. 4, 1975.

The compounds disclosed herein as cytoprotective agents have been disclosed as antiallergy agents and are described as anti-allergy oxamic acids or derivatives thereof. These compounds, together with their antiallergy uses and compositions, are described in U.S. Pat. Nos. 3,993,679; 4,159,278; 4,095,028; 4,089,973; 4,011,337; 4,091,011; 3,972,911; 4,067,995; 3,980,660; 4,044,148; 3,982,006; 4,061,791; 4,017,538; 4,119,783; 4,113,880; 4,128,660; 4,150,140; 3,966,965; 3,963,660; 4,038,398; 3,987,192; 3,852,324; and 3,836,541.

Certain antiallergy agents have been disclosed as gastric antisecretory agents see, e.g., U.S. Pat. Nos. 4,209,528 and 4,137,325.

Certain prostaglandins and prostaglandin analogs have been found useful in reducing gastric secretion and thus treating or preventing gastric or duodenal ulcers. See, e.g., U.S. Pat. Nos. 3,903,297 and 3,781,429. The prevention of gastric and duodenal erosive diseases (e.g., gastric and duodenal ulceration and erosive gastritis) with antacid or gastric antisecretory agents other than prostaglandins is likewise known in the art. See, for example, Mann, et al., Gastroenterology 68:A-88/945 (1945) which describes the use of metiamide (a gastric antisecretory agent) in preventing the gastric damage caused by the treatment of rats with aspirin and bile. See further, Mann, Gastroenterology 68:A-89/946 (1976) which describes the prevention of acute erosive gastritis by antacid administration.

However, gastric cytoprotection is different from gastric antisecretion and is an important pharmacological property. See, e.g., Robert, U.S. Pat. Nos. 4,097,603 "Gastric Cytoprotection with Nonantisecretory Doses of Prostaglandins"; Robert, "Cytoprotection by Prostaglandins," Gastroenterology 77:761–767 (1979); and Robert, et al., "Cytoprotection by Prostaglandins in Rats," Gastroenterology 77:433–443 (1979).

SUMMARY OF THE INVENTION

The present invention comprises a method of preventing a gastrointestinal disease in a mammal with high susceptibility to the aquisition of said disease, which comprises:

administering to said mammal systemically an amount effective to prevent the development of said disease of a compound of the formula I wherein $A_1$ is $=CR_2-$ or $=N-$;

wherein $R_1$ is hydrogen, $-NH-CO-CO-OR_4$, $-NH-CO-CO-N(CH_3)_2$, $-NO_2$ or $-NH_2$;

wherein $R_2$ is hydrogen, $-NO_2$, chloro, fluoro, bromo, $-COOH$, or $-C\equiv N$;

wherein $R_3$ is hydrogen, aceytl, carboxy, $-CF_3$, or $-C\equiv N$;

wherein $R_4$ is hydrogen or $(C_1-C_3)$alkyl;

wherein $R_5$ is hydrogen, hydroxy, or $-C\equiv N$; and wherein $R_6$ is hydrogen, $-NO_2$, or $-NH-CO-CO-OR_4$; and the pharmacologically acceptable acid addition salts thereof when $R_2$, $R_3$ or $R_5$ is $-C\equiv N$; with the following provisos:

(1) $A_1$ is $=N-$ only when $R_1$ is $-NH-CO-CO-OR_4$ and $R_2$, $R_3$, $R_5$ and $R_6$ are hydrogen;

(2) At least one of $R_2$, $R_3$, $R_5$ and $R_6$ is other than hydrogen; and (3) $R_6$ is $-NH-CO-CO-OH$ only when $R_1$ is not hydrogen.

The present invention includes the treatment of each of the various mammalian species, especially humans. With respect to nonhumans, the present invention is particularly and especially concerned with treating domesticated animals, for example, cattle, dogs, cats, and swine.

Any convenient route of administration is employed. Thus, oral formulation and oral administration is, for example, the preferred route for use in humans although parenteral (e.g., intravenous, intraperitoneal, and intramuscular) administration is also employed. See the U.S. Patents noted above under Prior Art for some appropriate and well known means for administering the compounds discussed herein.

With respect to the method described above, gastric and intestinal inflammatory diseases include specifically gastric ulcer, duodenal ulcer and gastritis, although other gastric inflammatory conditions, such as those secondary to radiation exposure, are likewise included within its purview. See U.S. Pat. No. 4,088,784 for a description of these sources of radiation for which the present invention provides cytoprotection. Gastrointestinal diseases caused by exposure to noxious chemical agents are also treated by the method of the present invention. Also included within the term "gastrointestinal diseases" which are prevented by the method of the present invention are the undesirable side effects produced by the administration of non-steroidal antiinflammatory (NOSAC) agents (which are prostaglandin synthetase inhibitors), as described in U.S. Pat. No. 3,917,828.

A further aspect of the present invention resides in the selection of patients for the present method who exhibit a high susceptibility to the acquisition of gastrointestinal inflammatory diseases. In accordance with the invention, patients who will benefit from these gastric cytoprotective compounds will fall into several classes.

First, patients with a previous history of gastric or duodenal ulcer are known to be highly susceptible to a recurrence of this disease, and thus the present invention provides a method for preventing or reducing recidivism in such ulcer-prone patients. Moreover, those with two or more episodes of gastric or duodenal ulcer, being particularly susceptible to the recurrence of gastric inflammatory diseases, are especially contemplated as subjects for the chronic administration of the gastric cytoprotective prostaglandins of the present invention.

A further class of subjects which exhibit a high susceptibility to the acquisition of gastrointestinal inflammatory disease are those experiencing stressful environmental conditions, whether of physical or emotional origin. Such subjects particularly include those persons whose emotional disposition has been identified as a source of recurrent gastritis or a prior episode of gastric or duodenal ulcer disease. Other such subjects include patients under severe physical conditions such as shock, sepsis, burns, multiple fractures, accident injuries with trauma (head, chest, abdomen, etc.), hemorrhage, extensive and prolonged surgical interventions, and organ transplants.

Further, patients for whom treatment by the present method is indicated include persons exhibiting chronic and excessive ethanol consumption. In particular, the use of the present method by persons diagnosed as alcoholics, according to standard methods for the diagnosis of this disease, are contemplated by the present method. Especially suitable candidates for the present method are those alcoholics with a history of recurrent or persistent gastritis resulting from uncontrolled or uncontrollable consumption of ethanol.

Further included as suitable subjects for treatment by the present method are humans exhibiting acute exposure to cytodestructive doses of ionizing radiations. While ionizing radiation from any source is contemplated, particularly suitable subjects include patients exposed accidentially to high levels of radiation and those receiving measured doses of radiation for therapeutic reasons (e.g., in the treatment of neoplastic diseases). Cytodestructive doses of such radiation are those capable of producing the symptoms of gastrointestinal distress associated with radiation sickness.

Further included as suitable subjects for treatment by the present method are humans exhibiting acute or chronic ingestive exposure of noxious, gastrointestinal cytodestructive or gastrointestinal cytotoxic chemical agents. Particularly contemplated by the present invention are those persons who suffer an accidental, acute exposure to poisons or other agents which are noxious or erosive to the gastrointestinal tissues. For example, children who ingest household chemicals, such as detergents, drain cleaners, and the like, are suitable subjects for treatment by the present method. In such an instance treatment is initiated following the usual emergency procedures, if any, which are indicated to control the systemic effects resulting from the ingested poison. Further included as suitable subjects for the present invention are those persons whose exposure to noxious gastrointestinal cytodestructive or gastrointestinal cytotoxic chemical agents is of a more chronic nature. For example, those persons whose occupation requires them to formulate or apply agricultural poisons (e.g., pesticides and herbicides) likewise are subjects for the present invention. In particular, such persons who are chronically exposed to these chemical agents and such chronic exposure has resulted in at least a single episode of gastritis or gastric or duodenal ulcer resulting therefrom are especially suitable for treatment in accordance with the present method. Further, humans exposed to therapeutic doses of chemotherapeutic agents used in the treatment of neoplastic diseases with known gastrointestinal cytotoxic or cytotoxic side effects provide further subjects for the present method.

Further included as suitable subjects for treatment by the present method are humans being treated with NOSAC such as aspirin, indomethacin, phenylbutazone, mefenamic acid, flufenamic acid, naproxen, 2-phenoxyphenylpropionic acid, (+)-3-chloro-4-cyclohexyl-α-methylphenylacetic acid, and ibuprofen.

Finally, the present invention is employed in subjects exhibiting a recent exposure to pathogens capable of producing diseases characterized by untoward gastric symptoms such as vomiting. Specifically contemplated by this application of the present invention are those persons who in travelling to foreign countries are likely to encounter or have encountered pathogens which have produced gastro-intestinal distress, and for whom a further exposure is contemplated.

The present invention requires administration of a dose of the compound effective to prevent the development of the gastrointestinal inflammatory disease. Thus, the dose required in accordance with the present invention is sufficiently great so as to permit the cytoprotective effect, but much smaller than those doses capable of producing any significant other effects.

The dosage regimen for the use of these compounds in accordance with this invention will depend on a variety of factors, including the type, age, weight, sex, and medical condition of the mammal, the nature and severity of the gastrointestinal disease and the particular compound to be administered. It is within the skill of the attending physician or veterinarian to determine the patient's susceptibility to the gastric disease, and to prescribe an effective amount of the phenylene dioxamic compound. In doing that, the physician or veterinarian would by one method start at a relatively low dose of the compound, for example, about 1 mg/kg/day to about 50 mg/kg/day, and observe the response of the patient for a few days. The dose is then adjusted downward or upward if necessary until the maximum effective dose is found. For example, the maximum need dose is usually between about 1 mg/kg/day and about 100 mg/kg/day although it may be necessary to occasionally exceed these doses when the susceptibility to the gastrointestinal disease is especially severe. Once the minimum effective dose of the particular phenylene dioxamic compound is determined for a particular subject, it is advantageous to provide the subject with the dosage schedule which will provide a substantially uniform level of the compound.

The most preferred compound of the present invention is the dioxamate N,N'-(2-chloro-5-cyano-m-phenylene)dioxamic acid (lodoxamide). Among lodoxamides preferred forms are the bis THAM (tris(hydroxymethyl)amino methane) salt and the diethyl ester, particularly the diethyl ester.

The preparation of the compounds used in the methods of the present invention is described in U.S. Patents noted above under Prior Art and the preparations of such compounds are incorporated by reference herein.

DESCRIPTION OF THE PREFERRED EMBODIMENTS

The efficacy of the compounds of the present invention as gastrointestinal cytoprotection agents is seen by the Example given below.

EXAMPLE

Female rats of an average body weight of 210 g were fasted for 24 hr. They were also deprived of water during the overnight period (from 3 p.m.), and placed in individual cylindrical stainless steel tubes to prevent coprophagy. On the following morning they were given 1.5 ml of various compounds orally at various doses of from 1 to 50 mg/kg.

The compounds were shaken overnight in water containing polysorbate 80 to obtain a fine suspension (one drop per 20 ml). Thirty minutes after treatment, 1 ml of absolute ethanol was given orally and the animals were killed with $CO_2$ 1 hr after the ethanol administration. Their stomachs were dissected out, opened along the greater curvature and randomized so that the examiner had no knowledge of the treatment given. They were examined with a 2×binocular magnifier for the presence of necrotic lesions. The number of necrotic lesions per stomach was recorded and the average number per group was calculated. Results were expressed as percent of control. The Dunnett two-tailed t-test (see Dunnett, "A Multiple Comparison Procedure for Comparing Several Treatments with Control," Amer. Stat. Assoc. 50:1096–1121 (1955)) was used for statistical analysis.

Table I shows the $ED_{50}$'s of some compounds within the scope of this invention.

TABLE I

| NAME | $ED_{50}$ mg/kg |
|---|---|
| 2',4'-dinitro-oxanilic acid, ethyl ester | ~50 |
| N,N'—(cyano-p-phenylene)dioxamic acid, diethyl ester | <50 |
| N,N'—2,6-pyridinediyldioxamic acid, compound (1:2) with 2-amino-2-(hydroxymethyl)-1,3-propanediol | ~50 |
| N,N'—[2-chloro-5-(trifluoromethyl)-m-phenylene]dioxamic acid | <25 |
| N,N'—(2-carboxy-m-phenylene)dioxamic acid, hydrate | ~50 |
| 2'-chloro-5'-cyano-oxanilic acid | <25 |
| N,N'—(4-cyano-m-phenylene)dioxamic acid | >25 |
| N,N'—m-phenylenedioxamic acid | >25 |
| N,N'—(2-chloro-m-phenylene)dioxamic acid | 25 |
| N,N'—(5-cyano-m-phenylene)dioxamic acid | <10 |
| 3'-amino-oxanilic acid, ethyl ester | >25 |
| N,N'—(5-acetyl-2-chloro-m-phenylene)-dioxamic acid | >25 |
| 3'-($N^2$,$N^2$—dimethyloxamido)oxanilic acid, ethyl ether | >25 |
| 3'-carboxy-2'-hydroxy-5'-nitro-oxanilic acid, ethyl ester hemihydrate | <10 |
| 2-benxothiazolyloxamic acid, ethyl ester | <10 |
| N,N'—(2-chloro-5-cyano-m-phenylene)-dioxamic acid (lodoxamide tromethamine) | <10 |

FORMULAS

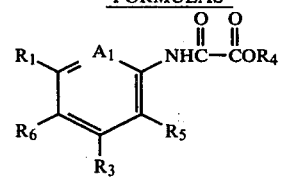

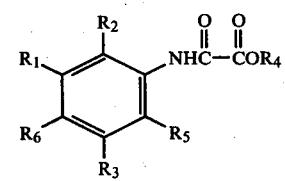

We claim:

1. A method for preventing gastrointestinal ulcers, in a mammal highly susceptible to said ulcers, due to one of the following conditions:
   (a) a previous history of gastric or duodenal ulcer,
   (b) stressful environmental conditions,
   (c) chronic and excessive alcohol consumption,
   (d) exposure to cytodestructive doses of ionizing radiation,
   (e) acute or chronic ingestion of noxious, gastrointestinal cytodestructive or gastrointestinal cytotoxic chemical agents,
   (f) treatment with non-steroidal antiinflammatory compounds (NOSAC), or
   (g) exposure to pathogens capable of producing untoward gastric symptoms; which comprises:
   administering systemically to said mammal an amount effective to prevent the development of said ulcers of a compound of the Formula I wherein $R_1$ is hydrogen, —NH—CO—CO—$OR_4$, —NH—CO—CO—N($CH_3$)$_2$, —$NO_2$ or —$NH_2$;
wherein $R_2$ is hydrogen, —$NO_2$, chloro, fluoro, bromo, —COOH, or —C≡N;
wherein $R_3$ is hydrogen, acetyl, carboxy, —$CF_3$, or —C≡N;
wherein $R_4$ is hydrogen or ($C_1$-$C_3$)alkyl;
wherein $R_5$ is hydrogen, hydroxy, or —C≡N; and
wherein $R_6$ is hydrogen, —$NO_2$, or —NH—(-CO—CO—$OR_4$; and the pharmacologically acceptable acid addition salts thereof when $R_2$, $R_3$ or $R_5$ is —C≡N; with the following provisos:
   (1) at least one of $R_2$, $R_3$, $R_5$ and $R_6$ is other than hydrogen and
   (2) $R_6$ is —NH—CO—CO—OH only when $R_1$ is not hydrogen.

2. A method of claim 4 wherein said mammal is a human and the compound of Formula I is selected from the group consisting of
2',4'-dinitro-oxanilic acid, ethyl ester;
N,N'-(cyano-p-phenylene)dioxamic acid, diethyl ester;
N,N'-[2-chloro-5-(trifluoromethyl)-m-phenylene]dioxamic acid; N,N'-(2-carboxy-m-phenylene)dioxamic acid, hydrate;
2'-chloro-5'-cyano-oxanilic acid;
N,N'-(4-cyano-m-phenylene)-dioxamic acid;
N,N'-m-phenylenedioxamic acid;
N,N'-(2-chloro-m-phenylene)dioxamic acid;
N,N'-(5-cyano-m-phenylene)dioxamic acid;
3'-amino-oxanilic acid, ethyl ester;
N,N'-(5-acetyl-2-chloro-m-phenylene)dioxamic acid;
3'-($N^2$,$N^2$-dimethyloxamido)oxanilic acid, ethyl ester;
3'-carboxy-2'-hydroxy-5'-nitro-oxanilic acid, ethyl ester, hemihydrate; and
N,N'-(2-chloro-5-cyano-m-phenylene)dioxamic acid.

3. A method of claim 3 wherein the compound is N,N'-(2-chloro-5-cyano-m-phenylene)-di-oxamic acid, (lodoxamide) its THAM salt or its ethyl ester.

* * * * *

UNITED STATES PATENT AND TRADEMARK OFFICE
CERTIFICATE OF CORRECTION

PATENT NO. : 4,439,445

DATED : March 27, 1984

INVENTOR(S) : Andre Robert, et al

It is certified that error appears in the above-identified patent and that said Letters Patent is hereby corrected as shown below:

Column 1, line 57, (1945) should read -- (1975) --.

Column 6, line 43, "wherein $R_6$ .... $-NH-(CO-CO-OR_4;$"
should read -- wherein $R_6$ .... $-NH-CO-CO-OR_4$ --.

Signed and Sealed this

Twelfth Day of February 1985

[SEAL]

Attest:

DONALD J. QUIGG

Attesting Officer

Acting Commissioner of Patents and Trademarks